United States Patent
Kwon et al.

(10) Patent No.: US 12,090,199 B2
(45) Date of Patent: Sep. 17, 2024

(54) H5N6 RECOMBINANT INFLUENZA VIRUS, A COMPOSITION FOR PREPARING THE SAME, AND A VACCINE COMPOSITION CONTAINING THE SAME

(71) Applicant: Seoul National University R&DB Foundation, Seoul (KR)

(72) Inventors: Hyuk Joon Kwon, Pyeongchang-gun (KR); Se Hee An, Seoul (KR); Seung Min Hong, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 119 days.

(21) Appl. No.: 17/547,406

(22) Filed: Dec. 10, 2021

(65) Prior Publication Data

US 2022/0202928 A1 Jun. 30, 2022

(30) Foreign Application Priority Data

Dec. 14, 2020 (KR) ........................ 10-2020-0174899

(51) Int. Cl.
| | |
|---|---|
| *A61K 39/145* | (2006.01) |
| *A61P 31/16* | (2006.01) |
| *A61P 37/04* | (2006.01) |
| *C07K 14/005* | (2006.01) |
| *C12N 7/00* | (2006.01) |
| *C12N 15/86* | (2006.01) |
| *A61K 39/00* | (2006.01) |

(52) U.S. Cl.
CPC ............ *A61K 39/145* (2013.01); *A61P 31/16* (2018.01); *A61P 37/04* (2018.01); *C07K 14/005* (2013.01); *C12N 7/00* (2013.01); *C12N 15/86* (2013.01); *A61K 2039/5254* (2013.01); *C12N 2760/16122* (2013.01); *C12N 2760/16134* (2013.01); *C12N 2760/16143* (2013.01)

(58) Field of Classification Search
None
See application file for complete search history.

(56) References Cited

FOREIGN PATENT DOCUMENTS

| KR | 100790801 B1 | 1/2008 |
|---|---|---|
| KR | 100862758 B1 | 10/2008 |
| KR | 101423695 B1 | 8/2014 |

OTHER PUBLICATIONS

An et al., Bioengineering a highly productive vaccine strain in embryonated chicken eggs and mammals from a non-pathogenic clade 2344 H5N8 strain, Vaccine, 2019, vol. 37, pp. 6154-6161.*
GenBank Accession BBB46330, haemagglutinin [Influenza A virus (A/chicken/Kumamoto/45/2016(H5N6))], 2017.*
GenBank Accession BBB46332, neuraminidase [Influenza A virus (A/chicken/Kumamoto/45/2016(H5N6))], 2017.*
The Program for the National High Pathogenicity AI Vaccination and Exit Strategy Development Final Report, Agriculture and Forestry Livestock Products Part (Feb. 14, 2018) (115 Pages).
Se-Hee An et al., Bioengineering a Highly Productive Vaccine Strain in Embryonated Chicken Eggs and Mammals from a Non-Pathogenic Clade 2•3•4•4 H5N8, Vaccine, Sep. 5, 2019, vol. 37, No. 42, pp. 6154-6161.
Jin-Wook Jang et al., Optimized Clade 2.3.2.1c H5N1 Recombinant-Vaccine Strains Against Highly Pathogenic Avian Influenza, J Vet Sci, 2017, vol. 18, No. S1, pp. 299-306.
Se-Hee An et al., Generation of Highly Productive and Mammalian Nonpathogenic Recombinant H9N2 Avian Influenza Viruses by Optimization of 3'end Promoter and NS Genome, Veterinary Microbiology, 2019, vol. 228, pp. 213-218.

* cited by examiner

*Primary Examiner* — Benjamin P Blumel
(74) *Attorney, Agent, or Firm* — Harness, Dickey & Pierce, P.L.C.

(57) ABSTRACT

The present invention relates to an mammalian non-pathogenic, highly-productive-in-embryonated-egg, heat-resistant, and attenuated clade 2.3.4.4c H5N6 recombinant influenza A virus, and a vaccine composition including the recombinant influenza virus and artificial H5 gene as active ingredients.

6 Claims, 5 Drawing Sheets

Specification includes a Sequence Listing.

[FIG. 1]

rH5N6  rH5N6-hmH103Y  rH5N6-hmH103Y-310PB2

PR8
01310
H5N6

[FIG. 2]
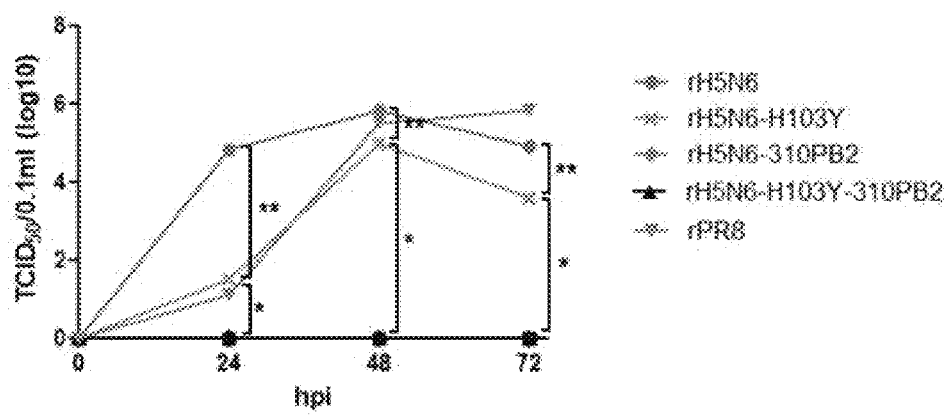
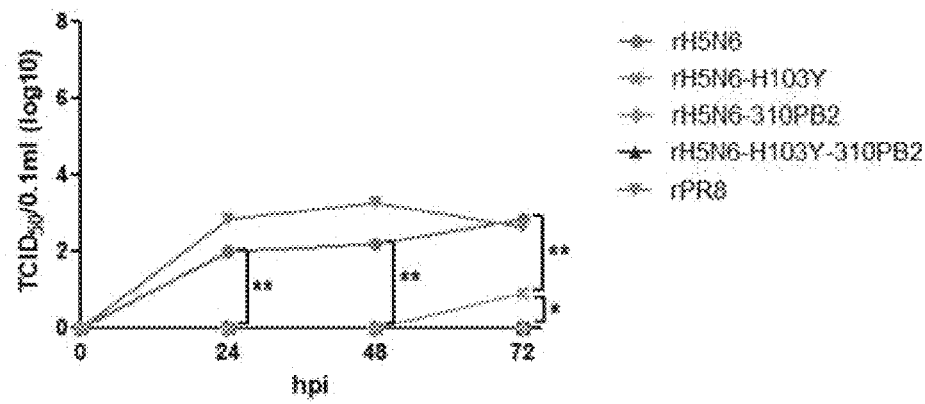

Inactivation pH test in MDCK

▲ rH5N6
☐ rH5N6-H103Y y-axis: $TCID_{50}/0.1ml$ (log10)
x-axis: pH

Inactivation pH test in ECEs

▲ rH5N6
☐ rH5N6-H103Y y-axis: HA titer (log2)
x-axis: pH

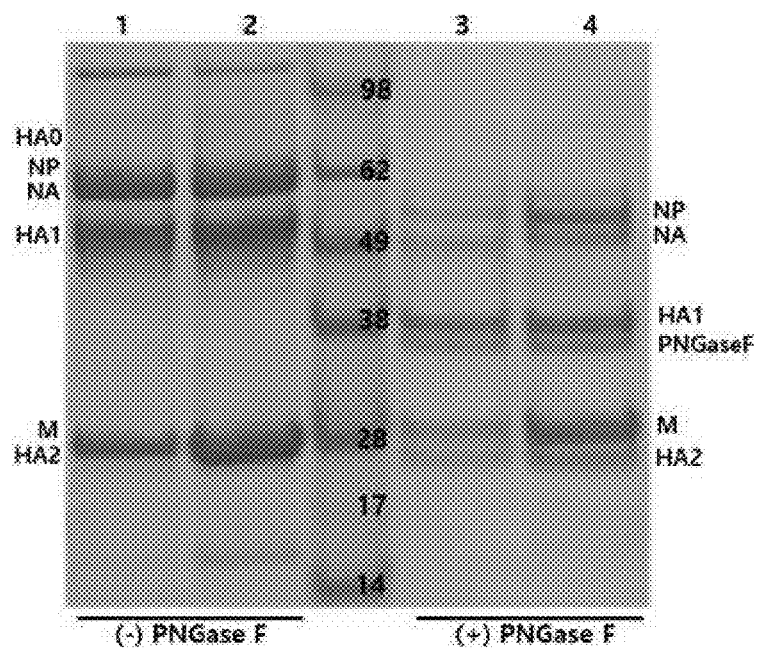
[FIG. 5]

SEQUENCE LISTING

```
<160> NUMBER OF SEQ ID NOS: 7

<210> SEQ ID NO 1
<211> LENGTH: 563
<212> TYPE: PRT
<213> ORGANISM: Artificial
<220> FEATURE:
<223> OTHER INFORMATION: H5N6 HA

<400> SEQUENCE: 1

Met Glu Lys Ile Val Leu Leu Leu Ala Val Val Ser Leu Val Lys Ser
1               5                   10                  15

Asp Gln Ile Cys Ile Gly Tyr His Ala Asn Asn Ser Thr Glu Gln Val
            20

```
                305                 310                 315                 320
Val Lys Ser Asn Lys Leu Val Leu Ala Thr Gly Leu Arg Asn Ser Pro
                325                 330                 335

Leu Ala Ser Gly Arg Gly Leu Phe Gly Ala Ile Ala Gly Phe Ile Glu
                340                 345                 350

Gly Gly Trp Gln Gly Met Val Asp Gly Trp Tyr Gly Tyr His His Ser
                355                 360                 365

Asn Glu Gln Gly Ser Gly Tyr Ala Ala Asp Arg Glu Ser Thr Gln Lys
                370                 375                 380

Ala Ile Asp Gly Val Thr Asn Lys Val Asn Ser Ile Ile Asp Lys Met
385                 390                 395                 400

Asn Thr Gln Phe Glu Ala Val Gly Arg Glu Phe Asn Asn Leu Glu Arg
                405                 410                 415

Arg Ile Glu Asn Leu Asn Lys Lys Met Glu Asp Gly Phe Leu Asp Val
                420                 425                 430

Trp Thr Tyr Asn Ala Glu Leu Leu Val Leu Met Glu Asn Glu Arg Thr
                435                 440                 445

Leu Asp Phe His Asp Ser Asn Val Lys Asn Leu Tyr Asp Lys Val Arg
                450                 455                 460

Leu Gln Leu Arg Asp Asn Ala Lys Glu Leu Gly Asn Gly Cys Phe Glu
465                 470                 475                 480

Phe Tyr His Lys Cys Asp Asn Glu Cys Met Glu Ser Val Arg Asn Gly
                485                 490                 495

Thr Tyr Asp Tyr Pro Gln Tyr Ser Glu Glu Ala Arg Leu Lys Arg Glu
                500                 505                 510

Glu Ile Ser Gly Val Lys Leu Glu Ser Ile Gly Thr Tyr Gln Ile Leu
                515                 520                 525

Ser Ile Tyr Ser Thr Val Ala Ser Ser Leu Ala Leu Ala Ile Ile Val
                530                 535                 540

Ala Gly Leu Ser Leu Trp Met Cys Ser Asn Gly Ser Leu Gln Cys Arg
545                 550                 555                 560

Ile Cys Ile
```

<210> SEQ ID NO 2
<211> LENGTH: 563
<212> TYPE: PRT
<213> ORGANISM: Artificial
<220> FEATURE:
<223> OTHER INFORMATION: H5N6 HA-H103Y

<400> SEQUENCE: 2

```
Met Glu Lys Ile Val Leu Leu Ala Val Val Ser Leu Val Lys Ser
1               5                   10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asp Ile
                35                  40                  45

Leu Glu Lys Thr His Asn Gly Arg Leu Cys Asp Leu Asn Gly Val Lys
                50                  55                  60

Pro Leu Ile Leu Lys Asp Cys Ser Val Ala Gly Trp Leu Leu Gly Asn
65                  70                  75                  80

Pro Met Cys Asp Glu Phe Ile Arg Val Pro Glu Trp Ser Tyr Ile Val
                85                  90                  95

Glu Arg Ala Asn Pro Ala Asn Asp Leu Cys Tyr Pro Gly Asn Leu Asn
                100                 105                 110
```

```
Asp Tyr Glu Glu Leu Lys Tyr Leu Leu Ser Arg Ile Asn His Phe Glu
            115                 120                 125

Lys Thr Leu Ile Ile Pro Lys Ser Ser Trp Pro Asn His Glu Thr Ser
130                 135                 140

Gly Val Ser Ala Ala Cys Pro Tyr Gln Gly Val Pro Ser Phe Phe Arg
145                 150                 155                 160

Asn Val Val Trp Leu Thr Lys Lys Asn Asp Ala Tyr Pro Thr Ile Lys
                165                 170                 175

Met Ser Tyr Asn Asn Thr Asn Gly Glu Asp Leu Leu Ile Leu Trp Gly
                180                 185                 190

Ile His His Ser Asn Asn Ala Ala Glu Gln Thr Asn Leu Tyr Lys Asn
                195                 200                 205

Pro Thr Thr Tyr Val Ser Val Gly Thr Ser Thr Leu Asn Gln Arg Leu
            210                 215                 220

Val Pro Lys Ile Ala Thr Arg Ser Gln Val Asn Gly Gln Gln Gly Arg
225                 230                 235                 240

Met Asp Phe Phe Trp Thr Ile Leu Lys Pro Asn Asp Ala Ile His Phe
                245                 250                 255

Glu Ser Asn Gly Asn Phe Ile Ala Pro Glu Tyr Ala Tyr Lys Ile Val
            260                 265                 270

Lys Lys Gly Asp Ser Thr Ile Met Lys Ser Glu Met Glu Tyr Gly His
            275                 280                 285

Cys Asn Thr Lys Cys Gln Thr Pro Ile Gly Ala Ile Asn Ser Ser Met
            290                 295                 300

Pro Phe His Asn Ile His Pro Leu Thr Ile Gly Glu Cys Pro Lys Tyr
305                 310                 315                 320

Val Lys Ser Asn Lys Leu Val Leu Ala Thr Gly Leu Arg Asn Ser Pro
                325                 330                 335

Leu Ala Ser Gly Arg Gly Leu Phe Gly Ala Ile Ala Gly Phe Ile Glu
                340                 345                 350

Gly Gly Trp Gln Gly Met Val Asp Gly Trp Tyr Gly Tyr His His Ser
            355                 360                 365

Asn Glu Gln Gly Ser Gly Tyr Ala Ala Asp Arg Glu Ser Thr Gln Lys
            370                 375                 380

Ala Ile Asp Gly Val Thr Asn Lys Val Asn Ser Ile Ile Asp Lys Met
385                 390                 395                 400

Asn Thr Gln Phe Glu Ala Val Gly Arg Glu Phe Asn Asn Leu Glu Arg
                405                 410                 415

Arg Ile Glu Asn Leu Asn Lys Lys Met Glu Asp Gly Phe Leu Asp Val
                420                 425                 430

Trp Thr Tyr Asn Ala Glu Leu Leu Val Leu Met Glu Asn Glu Arg Thr
            435                 440                 445

Leu Asp Phe His Asp Ser Asn Val Lys Asn Leu Tyr Asp Lys Val Arg
            450                 455                 460

Leu Gln Leu Arg Asp Asn Ala Lys Glu Leu Gly Asn Gly Cys Phe Glu
465                 470                 475                 480

Phe Tyr His Lys Cys Asp Asn Glu Cys Met Glu Ser Val Arg Asn Gly
                485                 490                 495

Thr Tyr Asp Tyr Pro Gln Tyr Ser Glu Glu Ala Arg Leu Lys Arg Glu
            500                 505                 510

Glu Ile Ser Gly Val Lys Leu Glu Ser Ile Gly Thr Tyr Gln Ile Leu
            515                 520                 525
```

```
Ser Ile Tyr Ser Thr Val Ala Ser Ser Leu Ala Leu Ala Ile Ile Val
            530                 535                 540

Ala Gly Leu Ser Leu Trp Met Cys Ser Asn Gly Ser Leu Gln Cys Arg
545                 550                 555                 560

Ile Cys Ile

<210> SEQ ID NO 3
<211> LENGTH: 459
<212> TYPE: PRT
<213> ORGANISM: Artificial
<220> FEATURE:
<223> OTHER INFORMATION: H5N6 NA

<400> SEQUENCE: 3

Met Asn Pro Asn Gln Lys Ile Thr Cys Ile Ser Ala Thr Gly Val Thr
1               5                   10                  15

Leu Ser Val Val Ser Leu Leu Ile Gly Ile Thr Asn Leu Gly Leu Asn
                20                  25                  30

Ile Gly Leu His Tyr Lys Val Ser Asp Ser Thr Thr Met Asn Ile Pro
            35                  40                  45

Asn Met Asn Glu Thr Asn Pro Thr Thr Thr Asn Ile Thr Asn Ile Ile
50                  55                  60

Met Asn Lys Asn Glu Glu Arg Thr Phe Leu Lys Leu Thr Lys Pro Leu
65                  70                  75                  80

Cys Glu Val Asn Ser Trp His Ile Leu Ser Lys Asp Asn Ala Ile Arg
                85                  90                  95

Ile Gly Glu Asp Ala His Ile Leu Val Thr Arg Glu Pro Tyr Leu Ser
            100                 105                 110

Cys Asp Pro Gln Gly Cys Arg Met Phe Ala Leu Ser Gln Gly Thr Thr
        115                 120                 125

Leu Arg Gly Gln His Ala Asn Gly Thr Ile His Asp Arg Ser Pro Phe
130                 135                 140

Arg Ala Leu Ile Ser Trp Glu Met Gly Gln Ala Pro Ser Pro Tyr Asn
145                 150                 155                 160

Thr Arg Val Glu Cys Ile Gly Trp Ser Ser Thr Ser Cys His Asp Gly
                165                 170                 175

Ile Ser Arg Met Ser Ile Cys Ile Ser Gly Pro Asn Asn Asn Ala Ser
            180                 185                 190

Ala Val Val Trp Tyr Arg Gly Arg Pro Val Thr Glu Ile Pro Ser Trp
        195                 200                 205

Ala Gly Asn Ile Leu Arg Thr Gln Glu Ser Glu Cys Val Cys His Lys
210                 215                 220

Gly Ile Cys Pro Val Val Met Thr Asp Gly Pro Ala Asn Ser Lys Ala
225                 230                 235                 240

Ala Thr Lys Ile Ile Tyr Phe Lys Glu Gly Lys Ile Gln Lys Thr Glu
                245                 250                 255

Glu Leu Gln Gly Asn Ala Gln His Ile Glu Glu Cys Ser Cys Tyr Gly
            260                 265                 270

Ala Ala Gly Met Ile Lys Cys Val Cys Arg Asp Asn Trp Lys Gly Ala
        275                 280                 285

Asn Arg Pro Ile Ile Thr Ile Asp Pro Glu Met Met Thr His Thr Ser
290                 295                 300

Lys Tyr Leu Cys Ser Lys Ile Leu Thr Asp Thr Ser Arg Pro Asn Asp
305                 310                 315                 320

Pro Thr Asn Gly Asn Cys Asp Ala Pro Ile Thr Gly Gly Ser Pro Asp
```

```
                325                 330                 335

Pro Gly Val Lys Gly Phe Ala Phe Leu Asp Gly Glu Asn Ser Trp Leu
            340                 345                 350

Gly Arg Thr Ile Ser Lys Asp Ser Arg Ser Gly Tyr Glu Met Leu Lys
        355                 360                 365

Val Pro Asn Ala Glu Ile Asp Thr Gln Ser Gly Pro Ile Ser Tyr Gln
    370                 375                 380

Leu Ile Val Asn Asn Gln Asn Trp Ser Gly Tyr Ser Gly Ala Phe Ile
385                 390                 395                 400
Asp Tyr Trp Ala Asn Lys Glu Cys Phe Asn Pro Cys Phe Tyr Val Glu
                405                 410                 415
Leu Ile Arg Gly Arg Pro Lys Glu Ser Gly Val Leu Trp Thr Ser Asn
            420                 425                 430

Ser Met Val Ala Leu Cys Gly Ser Arg Glu Arg Leu Gly Ser Trp Ser
        435                 440                 445

Trp His Asp Gly Ala Glu Ile Ile Tyr Phe Lys
    450                 455

<210> SEQ ID NO 4
<211> LENGTH: 758
<212> TYPE: PRT
<213> ORGANISM: Artificial
<220> FEATURE:
<223> OTHER INFORMATION: A/chicken/Korea/01310/2001(H9N2)-PB2

<400> SEQUENCE: 4

Glu Arg Ile Lys Glu Leu Arg Asp Leu Met Ser Gln Ser Arg Thr Arg
1               5                   10                  15
Glu Ile Leu Thr Lys Thr Thr Val Asp His Met Ala Ile Ile Lys Lys
            20                  25                  30

Tyr Thr Ser Gly Arg Gln Glu Lys Asn Pro Ala Leu Arg Met Lys Trp
        35                  40                  45

Met Met Ala Met Lys Tyr Pro Ile Thr Ala Asp Lys Arg Ile Met Glu
    50                  55                  60

Ile Ile Pro Glu Arg Asn Glu Gln Gly Gln Thr Leu Trp Ser Lys Thr
65                  70                  75                  80

Asn Asp Ala Gly Ser Asp Lys Val Met Val Ser Pro Leu Ala Val Thr
                85                  90                  95

Trp Trp Asn Arg Asn Gly Pro Thr Thr Ser Thr Ile His Tyr Pro Lys
            100                 105                 110

Val Tyr Lys Thr Tyr Phe Glu Lys Val Glu Arg Leu Lys His Gly Thr
        115                 120                 125

Phe Gly Pro Ile His Phe Arg Asn Gln Val Lys Ile Arg Arg Arg Val
    130                 135                 140

Asp Ile Asn Pro Gly His Ala Asp Leu Ser Ala Arg Glu Ala Gln Asp
145                 150                 155                 160

Val Ile Met Glu Val Val Phe Pro Asn Glu Val Gly Ala Arg Ile Leu
                165                 170                 175

Thr Ser Glu Ser Gln Leu Thr Ile Thr Lys Glu Lys Lys Glu Glu Leu
            180                 185                 190

Gln Asp Cys Lys Ile Ala Pro Leu Met Val Ala Tyr Met Leu Glu Arg
        195                 200                 205

Glu Leu Val Arg Lys Thr Arg Phe Leu Pro Val Ala Gly Gly Thr Ser
    210                 215                 220

Ser Val Tyr Ile Glu Val Leu His Leu Thr Gln Gly Thr Cys Trp Glu
```

```
            225                 230                 235                 240

Gln Met Tyr Thr Pro Gly Gly Glu Val Arg Asn Asp Val Asp Gln
                    245                 250                 255

Ser Leu Ile Ile Ala Ala Arg Asn Ile Val Arg Arg Ala Thr Val Ser
                    260                 265                 270

Ala Asp Pro Leu Ala Ser Leu Leu Glu Met Cys His Gly Thr Gln Ile
                    275                 280                 285

Gly Gly Ile Arg Met Val Asp Ile Leu Arg Gln Asn Pro Thr Glu Glu
                    290                 295                 300

Gln Ala Val Asp Ile Cys Lys Ala Ala Ile Gly Leu Arg Ile Ser Ser
    305                 310                 315                 320

Ser Phe Ser Phe Gly Gly Phe Thr Phe Lys Arg Thr Ser Gly Ser Ser
                    325                 330                 335

Val Lys Lys Glu Glu Val Leu Thr Gly Asn Leu Gln Thr Leu Lys
                    340                 345                 350

Ile Arg Val His Glu Gly Tyr Glu Glu Phe Thr Met Val Gly Arg Arg
                    355                 360                 365

Ala Thr Ala Leu Leu Arg Lys Ala Thr Arg Arg Leu Ile Gln Leu Ile
                    370                 375                 380

Val Ser Gly Arg Asp Glu Gln Ser Ile Ala Glu Ala Ile Ile Val Ala
    385                 390                 395                 400

Met Val Phe Ser Gln Glu Asp Cys Met Ile Lys Ala Val Arg Gly Asp
                    405                 410                 415

Leu Asn Phe Val Asn Arg Ala Asn Gln Arg Leu Asn Pro Met His Gln
                    420                 425                 430

Leu Leu Arg His Phe Gln Lys Asp Ala Lys Val Leu Phe Gln Asn Trp
                    435                 440                 445

Gly Ile Glu Pro Ile Asp Asn Val Met Gly Met Ile Gly Ile Leu Pro
                    450                 455                 460

Asp Met Thr Pro Ser Thr Glu Met Ser Leu Arg Gly Val Arg Val Ser
    465                 470                 475                 480

Lys Met Gly Val Asp Glu Tyr Ser Ser Thr Glu Arg Val Val Ser
                    485                 490                 495

Ile Asp Arg Phe Leu Arg Val Arg Asp Gln Arg Gly Asn Ile Leu Leu
                    500                 505                 510

Ser Pro Glu Glu Val Ser Glu Thr Gln Gly Thr Glu Lys Leu Thr Ile
                    515                 520                 525

Thr Tyr Ser Ser Ser Met Met Trp Glu Ile Asn Gly Pro Glu Ser Val
                    530                 535                 540

Leu Val Asn Thr Tyr Gln Trp Ile Ile Arg Asn Trp Glu Thr Val Lys
    545                 550                 555                 560

Ile Gln Trp Ser Gln Asp Pro Thr Met Leu Tyr Asn Lys Val Glu Phe
                    565                 570                 575

Glu Pro Phe Gln Ser Leu Val Pro Lys Ala Ala Arg Gly Gln Tyr Ser
                    580                 585                 590

Gly Phe Val Arg Thr Leu Phe Gln Gln Met Arg Asp Val Leu Gly Thr
                    595                 600                 605

Phe Asp Thr Val Gln Ile Ile Lys Leu Leu Pro Phe Ala Ala Ala Pro
                    610                 615                 620

Pro Glu Gln Ser Arg Met Gln Phe Ser Ser Leu Thr Val Asn Val Arg
    625                 630                 635                 640

Gly Ser Gly Met Arg Ile Leu Val Arg Gly Asn Ser Pro Val Phe Asn
                    645                 650                 655
```

```
Tyr Asn Lys Ala Thr Lys Arg Leu Thr Val Leu Gly Lys Asp Ala Gly
            660                 665                 670

Ala Leu Thr Glu Asp Pro Asp Glu Gly Thr Ala Gly Val Glu Ser Ala
        675                 680                 685

Val Leu Arg Gly Phe Leu Ile Leu Gly Lys Glu Asp Lys Arg Tyr Gly
    690                 695                 700

Pro Ala Leu Ser Ile Asn Glu Leu Ser Asn Leu Ala Lys Gly Glu Lys
705                 710                 715                 720

Ala Asn Val Leu Ile Gly Gln Gly Asp Val Val Leu Val Met Lys Arg
                725                 730                 735

Lys Arg Asp Ser Ser Ile Leu Thr Asp Ser Gln Thr Ala Thr Lys Arg
            740                 745                 750

Ile Arg Met Ala Ile Asn
        755

<210> SEQ ID NO 5
<211> LENGTH: 498
<212> TYPE: PRT
<213> ORGANISM: Artificial
<220> FEATURE:
<223> OTHER INFORMATION: A/wild duck/Korea/SNU50-5/2009(H5N1)-NP

<400> SEQUENCE: 5

Met Ala Ser Gln Gly Thr Lys Arg Ser Tyr Glu Gln Met Glu Thr Gly
1               5                   10                  15

Gly Glu Arg Gln Asn Ala Thr Glu Ile Arg Ala Ser Val Gly Arg Met
            20                  25                  30

Val Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Arg Asp Gly Lys Trp Met Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Leu Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255
```

```
        Ile Phe Leu Ala Arg Ser Ala Leu Ile Leu Arg Gly Ser Val Ala His
                        260                 265                 270

Lys Ser Cys Leu Pro Ala Cys Val Tyr Gly Leu Ala Val Ala Ser Gly
                        275                 280                 285

Tyr Asp Phe Glu Arg Glu Gly Tyr Ser Leu Val Gly Ile Asp Pro Phe
                        290                 295                 300

Arg Leu Leu Gln Asn Ser Gln Val Phe Ser Leu Ile Arg Pro Asn Glu
        305                 310                 315                 320

Asn Pro Ala His Lys Ser Gln Leu Val Trp Met Ala Cys His Ser Ala
                        325                 330                 335

Ala Phe Glu Asp Leu Arg Val Ser Ser Phe Ile Arg Gly Thr Arg Val
                        340                 345                 350

Val Pro Arg Gly Gln Leu Ser Thr Arg Gly Val Gln Ile Ala Ser Asn
                        355                 360                 365

Glu Asn Met Glu Thr Met Asp Ser Ser Thr Leu Glu Leu Arg Ser Arg
                        370                 375                 380

Tyr Trp Ala Ile Arg Thr Arg Ser Gly Gly Asn Thr Asn Gln Gln Arg
        385                 390                 395                 400

Ala Ser Ala Gly Gln Ile Ser Val Gln Pro Thr Phe Ser Val Gln Arg
                        405                 410                 415

Asn Leu Pro Phe Glu Arg Ala Thr Ile Met Ala Ala Phe Thr Gly Asn
                        420                 425                 430

Thr Glu Gly Arg Thr Ser Asp Met Arg Thr Glu Ile Ile Arg Met Met
                        435                 440                 445

Glu Ser Ala Arg Pro Glu Asp Val Ser Phe Gln Gly Arg Gly Val Phe
                        450                 455                 460

Glu Leu Ser Asp Glu Lys Ala Thr Asn Pro Ile Val Pro Ser Phe Asp
        465                 470                 475                 480

Met Ser Asn Glu Gly Ser Tyr Phe Phe Gly Asp Asn Ala Glu Glu Tyr
                        485                 490                 495

Asp Asn

<210> SEQ ID NO 6
<211> LENGTH: 265
<212> TYPE: PRT
<213> ORGANISM: Artificial
<220> FEATURE:
<223> OTHER INFORMATION: (A/chicken/Korea/KBNP-0028/00(H9N2)-NS
<220> FEATURE:
<221> NAME/KEY: MISC_FEATURE
<222> LOCATION: (231)..(231)
<223> OTHER INFORMATION: X is a position encoded by a stop codon (i.e.,
      absence).
<220> FEATURE:
<221> NAME/KEY: MISC_FEATURE
<222> LOCATION: (243)..(243)
<223> OTHER INFORMATION: X is a position encoded by a stop codon (i.e.,
      absence).
<220> FEATURE:
<221> NAME/KEY: MISC_FEATURE
<222> LOCATION: (252)..(252)
<223> OTHER INFORMATION: X is a position encoded by a stop codon (i.e.,
      absence).
<220> FEATURE:
<221> NAME/KEY: MISC_FEATURE
<222> LOCATION: (265)..(265)
<223> OTHER INFORMATION: X is a position encoded by a stop codon (i.e.,
      absence).

<400> SEQUENCE: 6

Met Asp Ser Asn Thr Val Ser Ser Phe Gln Val Asp Cys Phe Leu Trp
```

```
1               5                   10                  15
His Val Arg Lys Arg Phe Ala Asp Gln Glu Leu Gly Asp Ala Pro Phe
                20                  25                  30
Leu Asp Arg Leu Arg Arg Asp Gln Lys Ser Leu Arg Gly Arg Gly Ser
                35                  40                  45
Thr Leu Gly Leu Asp Ile Glu Thr Ala Thr Arg Gly Gly Lys Gln Ile
                50                  55                  60
Val Glu Arg Ile Leu Phe Lys Glu Ser Asp Glu Ala Leu Lys Met Thr
65                  70                  75                  80
Val Ala Ser Val Pro Ala Thr Arg Tyr Leu Thr Asp Met Thr Leu Glu
                85                  90                  95
Glu Met Ser Arg Asp Trp Phe Met Leu Met Pro Lys Gln Lys Val Ala
                100                 105                 110
Gly Ser Leu Cys Ile Lys Ile Asp Gln Ala Ile Met Asp Lys Thr Ile
                115                 120                 125
Thr Leu Lys Ala Asn Phe Ser Val Thr Phe Gly Arg Leu Glu Thr Leu
                130                 135                 140
Ile Leu Leu Arg Ala Phe Ser Glu Glu Gly Ala Ile Val Gly Glu Ile
145                 150                 155                 160
Ser Pro Leu Pro Ser Leu Pro Gly His Thr Asp Glu Asp Val Lys Asn
                165                 170                 175
Ala Ile Gly Val Leu Ile Gly Gly Leu Glu Trp Asn Asn Asn Thr Val
                180                 185                 190
Arg Val Ser Glu Thr Leu Gln Arg Phe Ala Trp Arg Ser Ser Asp Glu
                195                 200                 205
Asn Gly Arg Pro Pro Leu Pro Pro Lys Gln Lys Gln Lys Met Ala Arg
                210                 215                 220
Thr Ile Gly Ser Glu Val Xaa Arg Asn Lys Val Ala Asp Arg Arg Gly
225                 230                 235                 240
Ala Thr Xaa Ile Lys Asp Tyr Gly Glu Gln Leu Xaa Thr Asn Asn Ile
                245                 250                 255
Tyr Ala Ser Leu Thr Thr Ile Ala Xaa
                260                 265
```

<210> SEQ ID NO 7
<211> LENGTH: 316
<212> TYPE: PRT
<213> ORGANISM: Artificial
<220> FEATURE:
<223> OTHER INFORMATION: A/chicken/Korea/01310/2001(H9N2)-M
<220> FEATURE:
<221> NAME/KEY: MISC_FEATURE
<222> LOCATION: (253)..(253)
<223> OTHER INFORMATION: X is a position encoded by a stop codon (i.e.,
      absence).
<220> FEATURE:
<221> NAME/KEY: MISC_FEATURE
<222> LOCATION: (273)..(273)
<223> OTHER INFORMATION: X is a position encoded by a stop codon (i.e.,
      absence).
<220> FEATURE:
<221> NAME/KEY: MISC_FEATURE
<222> LOCATION: (285)..(285)
<223> OTHER INFORMATION: X is a position encoded by a stop codon (i.e.,
      absence).
<220> FEATURE:
<221> NAME/KEY: MISC_FEATURE
<222> LOCATION: (299)..(299)
<223> OTHER INFORMATION: X is a position encoded by a stop codon (i.e.,
      absence).
<220> FEATURE:
<221> NAME/KEY: MISC_FEATURE -continued

```
<222> LOCATION: (316)..(316)
<223> OTHER INFORMATION: X is a position encoded by a stop codon (i.e.,
      absence).

<400> SEQUENCE: 7

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
            35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
                85                  90                  95

Val Lys Leu Tyr Arg Lys Leu Arg Glu Ile Thr Phe His Gly Ala
                100                 105                 110

Lys Glu Val Ala Leu Ser Tyr Ser Thr Gly Ala Leu Ala Ser Cys Met
            115                 120                 125

Gly Leu Ile Tyr Asn Arg Met Gly Thr Val Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Ala Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
            195                 200                 205

Ala Arg Gln Met Val Gln Ala Met Arg Thr Ile Gly Thr His Pro Ser
    210                 215                 220

Ser Ser Ala Gly Leu Lys Asp Asp Leu Leu Glu Asn Leu Gln Ala Tyr
225                 230                 235                 240

Gln Lys Arg Met Gly Val Gln Ile Gln Arg Phe Lys Xaa Thr Ser Arg
                245                 250                 255

Tyr Cys Arg Lys Tyr His Trp Asp Leu Ala Leu Asp Ile Val Asp Ser
            260                 265                 270

Xaa Ser Ser Phe Leu Gln Met His Leu Ser Ser Pro Xaa Ile Arg Phe
            275                 280                 285

Glu Lys Arg Ala Phe Tyr Gly Arg Ser Ala Xaa Val Tyr Glu Gly Arg
    290                 295                 300

Val Ser Thr Gly Thr Ala Glu Cys Cys Gly Cys Xaa
305                 310                 315
```

H5N6 RECOMBINANT INFLUENZA VIRUS, A COMPOSITION FOR PREPARING THE SAME, AND A VACCINE COMPOSITION CONTAINING THE SAME

CROSS-REFERENCE TO RELATED APPLICATION

This application claims priority to and the benefit of Korean Patent Application No. 10-2020-0174899, filed on Dec. 14, 2020, the disclosure of which is incorporated herein by reference in its entirety.

SEQUENCE LISTINGS

This application contains various sequence listings (i.e., SEQ ID NO: 1, SEQ ID NO: 2, SEQ ID NO: 3, SEQ ID NO: 4, SEQ ID NO: 5, SEQ ID NO: 6, and SEQ ID NO: 7) that are included in an ASCII text file entitled "SOP11583US_sequence listing" created on Mar. 16, 2022, having a file size of 31 kilobytes that is incorporated by reference herein in its entirety.

TECHNICAL FIELD

The present invention relates to an H5N6 recombinant influenza virus, a composition for preparing the same, and a vaccine composition containing the same.

BACKGROUND ART

Influenza virus belongs to orthomyxovirus, and as a virus having 8 negative single-stranded RNA fragments as a genome, hem agglutinin (HA), neuraminidase (NA), nucleocapsid protein (nucleoprotein; NP), matrix proteins 1 and 2 (matrix, M1, M2), polymerase subunits A, B1, and B2 (PA, PB1, and PB2, respectively), and nonstructural proteins 1 and 2 (NS1 and NS2, respectively) are made from the 8 RNA fragments.

Currently, in Korea, the low pathogenic avian influenza 01310 is used as a inactivated vaccine by inactivating 01310 CE20, which is passaged 20 times in 10-day-old embryonated eggs, and even though the highly pathogenic avian influenza vaccine is not vaccinated, antigens are stocked for emergency vaccine production in case of emergency. However, in China and other countries with highly pathogenic avian influenza, in order to prevent highly pathogenic and epidemic avian influenza, 6 internal genes of PR8 and the HA gene of the highly pathogenic virus are attenuated through the reverse genetics technology, and the virus is harvested by recombination with the NA gene, propagated in embryonated eggs, inactivated, and used as a inactivated vaccine.

Recombinant influenza A vaccine using reverse genetics technology is being used in the form of a recombinant virus created by transforming and transfecting (Korean Patent No. 0862758) 8 plasmids by cloning 8 genomes such as PR8 virus and A/Ann Arbor/6/60 (H2N2) virus, which is a cold-adapted attenuator of A/WSN/33 (H1N1) virus with excellent proliferation in chicken embryos and well-known characteristics, into a bidirectional reverse genetics vector in which viral genome transcription takes place in one direction of the vector and mRNA is produced in the other direction. In general, the HA and NA genes are amplified from a recently epidemic virus by RT-PCR, cloned into a reverse genetics vector, and transfected with the remaining 6 genes of PR8 to create a vaccine strain, and a inactivated vaccine is produced by inactivating the virus.

Certain subtypes of recombinant highly pathogenic avian influenza viruses produced using PR8 internal genes may have poor proliferation in embryonated eggs, and since PR8 is a human influenza A virus, there is a risk of cross infection between birds and humans. In particular, in the case of the PB2 gene, PR8 has amino acid mutations related to mammalian pathogenicity (E627K, A199S, A674T, T271A, and A588I), whereas in the case of the PB2 gene of A/chicken/Korea/01310/2001(H9N2) (01310), which is a low pathogenic H9N2 avian influenza virus, it was confirmed that pathogenicity in mammals disappears (Kim et al., 2014) when it is recombined with PR8 and inoculated into mice, and when this recombinant expression vector (Korean Patent No. KR101423695B1) is used, it is possible to prepare a highly-productive-in-embryonated-egg and mammalian non-pathogenic recombination virus.

A/wild duck/Korea/SNU50-5/2009 (H5N1) (SNU50-5), which is an H5N1 low pathogenic avian influenza virus, had low proliferation in embryonated eggs, but the proliferative property in embryonated eggs was improved through 20 passages of embryonated eggs. In this process, 4 mutations in the HA protein (HA1; H103Y, K161E and L317P, HA2; R51K) and one mutation in the NA protein (S369N) were obtained, and these mutations were confirmed to increase the proliferative property of SNU50-5 (Kim, et al., 2013). The H103Y mutation of the H5N1 virus HA protein is known to be important for mammalian pathogenicity because it increases acid resistance and heat resistance, thereby maintaining the ability to infect the mammalian upper respiratory tract at low pH, and thereby increasing the likelihood of horizontal transmission by droplets (Linster, et al., 2014; Zhang, et al., 2013). When the above four mutations were applied to the highly pathogenic clade 2.3.4.4b H5N6 influenza A virus, it was confirmed that the proliferative property and heat resistance in embryonated eggs was increased when the H103Y mutation was applied (An, Lee, et al. 2019).

The highly pathogenic clade 2.3.4.4c H5N6 influenza A virus caused tremendous economic damage in Korea, and the Animal and Plant Quarantine Agency has selected a vaccine strain for prevention in emergencies, and domestic animal vaccine companies produce the virus for vaccine production as a raw material and maintain in a frozen state. However, clade 2.3.4.4c H5N6 vaccine strain constructed using conventional reverse genetics technology has a high proliferative titer in embryonated eggs, but when inoculated with the actual inactivated vaccine, the antibody titer is low compared to the proliferative titer, and thus, there was a problem of low immunogenicity of vaccines. In the recombinant virus using the existing reverse genetics system, there is a problem that all of 6 internal genes are derived from H1N1 virus, and the T cell epitope sequence, which is important for cellular immunity, has a low coincidence rate with the genes of the highly pathogenic avian influenza virus.

DISCLOSURE

Technical Problem

An H5N6 recombinant influenza virus is provided.
A composition for preparing an H5N6 recombinant influenza virus or a preparation method using the same is provided.

A cell transformed with the composition for preparing an H5N6 recombinant influenza virus is provided.

A vaccine composition including the H5N6 recombinant influenza virus is provided.

Technical Solution

An aspect may provide an H5N6 recombinant influenza virus, including a hemagglutinin (HA) protein of influenza virus H5N6 strain; neuraminidase (NA) of H5N6 strain; polymerase subunit B2 (PB2) of low pathogenic influenza virus; and one or more proteins selected from the group consisting of polymerase subunit B1 (PB1), polymerase subunit A (PA), nucleocapsid (nucleoprotein: NP), matrix protein (matrix: M), and nonstructural protein (NS) of influenza virus H1N1 strain.

The present inventors collected the sequence of the highly pathogenic clade 2.3.4.4c H5N6 avian influenza virus isolated from outdoors and artificially synthesized the HA and NA proteins with the most frequent sequences, and after mutating the $103^{rd}$ histidine (H) codon of the HA protein to the tyrosine (Y) codon, the PB2 gene of the PR8 virus was replaced with the PB2 gene of 01310 to construct a clade 2.3.4.4c H5N6 recombinant virus. In order to confirm the proliferative property of the recombinant virus in embryonated eggs, 10-day-old embryonated eggs were inoculated with 100 $EID_{50}/0.1$ mL for each, and when the $103^{rd}$ amino acid of the HA protein was mutated from histidine to tyrosine, the HA protein lost its activity in a low pH environment, resulting in loss of the proliferative property in embryonated eggs and mammalian-derived cell lines. Even when the PB2 gene of PR8 was substituted with the PB2 gene of 01310, it was confirmed that while maintaining high proliferation in embryonated eggs, there was no proliferation in mammalian-derived cell lines and mice, thereby confirming avirulence in mammals. In addition, even when the recombinant virus was heat-treated at 55° C. for 90 minutes, it was confirmed that the hemagglutination titer did not decrease at all, confirming that it had heat resistance. In addition, the virus protein content obtained through ultracentrifugation was higher, and the antigen content was excellent, confirming that when it was inactivated using binary ethyleneimine (BEI) and inoculated to 3-week-old chickens and 2-week-old ducks with an oil emulsion vaccine, the formed antibody titer was increased. In addition, by applying the H103Y mutation, the fusion pH of the HA protein, which affects the proliferative property in mammals, was increased, further eliminating the risk of transmission to mammals.

Although the vaccine in which the NP and M genes, which are known to be important for hetero-subtypic protection because they have a relatively conservative sequence, were changed to avian influenza virus-derived genes, the titer was low, but it was confirmed that the amount of virus released when the internal genes matched was further reduced, confirming that it further stimulated cellular immunity, which is important for viral clearance. The recombinant influenza virus of the present invention was confirmed to have high proliferation in embryonated eggs and avirulence in mammals as well as heat resistance, and the present invention was completed by confirming high immunogenicity by confirming the improved antibody-forming ability as a result of inoculating chickens with an oil emulsion vaccine because the antigen amount of the virus isolated by ultracentrifugation was higher and inactivated.

Influenza virus is a virus of the Orthomyxoviridae family and may cause flu or a seasonal common cold. The influenza virus may be a clade 2.3.4.4c H5N6 virus. The influenza virus H5N6 strain is referred to as influenza A virus subtype H5N6. Hemagglutinin (HA) protein is also referred to as hemagglutination protein or hemagglutinin. The hemagglutinin protein may be a polypeptide including the amino acid sequence of SEQ ID NO: 1 or 2. The hemagglutinin protein may be that the $103^{rd}$ amino acid from the N-terminus is mutated in the amino acid sequence of SEQ ID NO: 1. The hemagglutinin protein may be that histidine (H), which is the $103^{rd}$ amino acid from the N-terminus in the amino acid sequence of SEQ ID NO: 1, is mutated to tyrosine (Y).

Neuraminidase (NA) refers to an enzyme that hydrolyzes neuraminic acid to separate sialic acid. The neuraminidase may be required when the virus enters or exits the host's cells. The neuraminidase may be neuraminidase derived from the influenza virus H5N6 strain. The neuraminidase may be a polypeptide including the amino acid sequence of SEQ ID NO: 3.

The low pathogenic influenza virus may be A/chicken/Korea/01310/2001 (H9N2) (hereinafter, referred to as '01310') (Korean Patent No. 0790801), which is a low pathogenic avian influenza virus in Korea. The 01310 strain is a domestic isolated strain, which is isolated as in Example 1 of Korean Patent No. 0790801, and has low pathogenicity. However, although it is low pathogenic, since the 01310 strain is a pathogenic virus, it cannot be deposited in a depository institution, and is currently being stored in the Bird Disease Division of the Animal and Plant Quarantine Agency. Polymerase subunit B2 is one of the subunits of the RNA-dependent RNA polymerase of influenza virus. The polymerase subunit B2 (PB2) protein may be a polypeptide including the amino acid sequence of SEQ ID NO: 4.

The influenza virus H1N1 strain may be A/Puerto Rico/8/34 (hereinafter, referred to as 'PR8').

Polymerase subunit B1 (PB1) is one of the subunits of the RNA-dependent RNA polymerase of influenza virus. The polymerase subunit B1 may be a polypeptide encoded by the nucleic acid sequence of GenBank accession number NC 002021 or a polypeptide including the amino acid sequence of Uniprot P03431.

Nucleocapsid (nucleoprotein: NP) is a structural protein that encapsulates the negative strand virus RNAfmf. The nucleocapsid may be a polypeptide encoded by the nucleic acid sequence of GenBank accession number NC 002019 or a polypeptide including the amino acid sequence of Uniprot P03466.

Matrix protein (M) is a structural protein that connects the viral core and the viral envelope. The matrix protein may be a polypeptide encoded by the nucleic acid sequence of GenBank accession number NC 002016 or a polypeptide including the amino acid sequence of Uniprot P06821 or P03485.

Nonstructural protein (NS) is a homodimeric RNA-binding protein required for viral replication. The nonstructural protein may be a polypeptide encoded by the nucleic acid sequence of GenBank accession number NC 002020 or a polypeptide including the amino acid sequence of Uniprot P03496.

The H5N6 recombinant influenza virus may include one or more proteins selected from the group consisting of polymerase subunit B1, polymerase subunit A, nucleocapsid, matrix protein, and nonstructural protein of influenza virus H1N1 strain. The H5N6 recombinant influenza virus may include all of polymerase subunit B1, polymerase subunit A, nucleocapsid, matrix protein, and nonstructural protein of the influenza virus H1N1 strain.

The H5N6 recombinant influenza virus was deposited on Aug. 4, 2020, and given Accession No. KCTC14261BP by the Korean Collection for Type Cultures located at Korea Research Institute of Bioscience and Biotechnology (KRIBB), 181, Ipsin-gil, Jeongeu-si, Jeolllabuk-do 56212, Republic of Korea.

The H5N6 recombinant influenza virus may be a recombinant virus including two or more of H5N6 strain-derived protein, low pathogenic influenza virus-derived protein, and H1N1 strain-derived protein.

The H5N6 recombinant influenza virus may be an mammalian non-pathogenic, highly-productive-in-embryonated-egg, and heat-resistant virus. The H5N6 recombinant influenza virus may be an mammalian non-pathogenic, highly-productive-in-embryo egg, heat-resistant, and attenuated clade 2.3.4.4c H5N6 recombinant influenza A virus. The H5N6 recombinant influenza virus is safe because it is not pathogenic in mammals and has an excellent amount of antigen production in embryonated eggs, and therefore, it is very useful because it may increase the productivity of vaccines and antibody formation. In addition, it has high heat resistance, and thus, it is useful for storing raw materials/products of vaccines and extending the distribution period.

An aspect may provide an H5N6 recombinant influenza virus, including one or more proteins selected from the group consisting of: a hemagglutinin (HA) protein of influenza virus H5N6 strain, wherein the hemagglutinin protein is a hemagglutinin protein in which the $103^{rd}$ amino acid from the N-terminus is mutated in the amino acid sequence of SEQ ID NO: 1; neuraminidase (NA) of influenza virus H5N6 strain; polymerase subunit B2 (PB2) and matrix protein (M) of low pathogenic influenza virus; polymerase subunit B1 (PB1) and polymerase subunit A (PA) of influenza virus H1N1 strain; nucleocapsid (nucleoprotein: NP) of influenza virus H5N1 strain; and nonstructural protein (NS) of influenza virus H9N2.

Recombinant clade 2.3.4.4c H5N6 virus, in which the internal genes were substituted with the NP gene of SNU50-5 (SEQ ID NO: 5), which is a low pathogenic avian influenza virus, the NS gene of 0028 (SEQ ID NO: 6), and the M gene of 01310 (SEQ ID NO: 7), was constructed, and it was confirmed that the immunogenicity of the recombinant vaccine with the substituted internal genes was further improved by confirming that the amount of virus released after attacking and inoculating the outdoor strain virus A/Mandarin duck/Korea/K16-187-3/2016 (H5N6), which differs only in the internal genes, was less.

Influenza virus is a virus of the Orthomyxoviridae family and may cause flu or a seasonal common cold. The influenza virus may be a clade 2.3.4.4c H5N6 virus. The influenza virus H5N6 strain is referred to as influenza A virus subtype H5N6.

Hemagglutinin (HA) protein is also referred to as hemagglutination protein or hemagglutinin. The hemagglutinin protein may be a polypeptide including the amino acid sequence of SEQ ID NO: 1 or 2. The hemagglutinin protein may be that the $103^{rd}$ amino acid from the N-terminus is mutated in the amino acid sequence of SEQ ID NO: 1. The hemagglutinin protein may be that histidine (H), which is the $103^{rd}$ amino acid from the N-terminus in the amino acid sequence of SEQ ID NO: 1, is mutated to tyrosine (Y).

Neuraminidase (NA) refers to an enzyme that hydrolyzes neuraminic acid to separate sialic acid. The neuraminidase may be required when the virus enters or exits the host's cells. The neuraminidase may be neuraminidase derived from the influenza virus H5N6 strain. The neuraminidase may be a polypeptide including the amino acid sequence of SEQ ID NO: 3.

The low pathogenic influenza virus may be A/chicken/Korea/01310/2001 (H9N2) (hereinafter, referred to as '01310') (Korean Patent No. 0790801), which is a low pathogenic avian influenza virus in Korea. The 01310 strain is a domestic isolated strain, which is isolated as in Example 1 of Korean Patent No. 0790801, and has low pathogenicity. However, although the 01310 strain is low pathogenic, since it is a pathogenic virus, it cannot be deposited in a depository institution, and is currently being stored in the Bird Disease Division of the Animal and Plant Quarantine Agency. Polymerase subunit B2 is one of the subunits of the RNA-dependent RNA polymerase of influenza virus. The polymerase subunit B2 (PB2) protein may be a polypeptide including the amino acid sequence of SEQ ID NO: 4. The matrix protein (matrix: M) is a structural protein that connects the viral core and the viral envelope. The matrix protein (matrix: M) may be a polypeptide including the amino acid sequence of SEQ ID NO: 7.

The influenza virus H1N1 strain may be A/Puerto Rico/8/34 (hereinafter, referred to as 'PR8').

Polymerase subunit B1 (PB1) is one of the subunits of the RNA-dependent RNA polymerase of influenza virus. The polymerase subunit B1 may be a polypeptide encoded by the nucleic acid sequence of GenBank accession number NC_002021 or a polypeptide including the amino acid sequence of Uniprot P03431.

Polymerase subunit A (PA) is one of the subunits of the RNA-dependent RNA polymerase of the influenza virus. The polymerase subunit A may be a polypeptide encoded by the nucleic acid sequence of GenBank accession number NC_002022 or a polypeptide including the amino acid sequence of Uniprot P03433.

Nucleocapsid (nucleoprotein: NP) is a structural protein that encapsulates the negative strand virus RNAfmf. The nucleocapsid (nucleoprotein: NP) may be a polypeptide including the amino acid sequence of SEQ ID NO: 5.

Nonstructural protein (NS) is a homodimeric RNA-binding protein required for viral replication. The nonstructural protein (NS) may be a polypeptide including the amino acid sequence of SEQ ID NO: 6.

The H5N6 recombinant influenza virus was deposited on Nov. 27, 2020, and given Accession No. KCTC14391BP by the Korean Collection for Type Cultures located at Korea Research Institute of Bioscience and Biotechnology (KRIBB), 181, Ipsin-gil, Jeongeu-si, Jeolllabuk-do 56212, Republic of Korea.

The H5N6 recombinant influenza virus may be a recombinant virus including two or more of influenza virus H5N6 strain-derived protein, low pathogenic influenza virus-derived protein, influenza virus H1N1 strain-derived protein, influenza virus H5N1 strain-derived protein, and influenza virus H9N2 strain-derived protein.

Another aspect provides a composition for preparing an H5N6 recombinant influenza virus, including a polynucleotide encoding a hemagglutinin protein of influenza virus H5N6 strain; a polynucleotide encoding neuraminidase of H5N6 strain; a polynucleotide encoding polymerase subunit B2 of low pathogenic influenza virus; and a polynucleotide encoding one or more proteins selected from the group consisting of polymerase subunit B1, polymerase subunit A, nucleocapsid, matrix protein, and nonstructural protein of influenza virus H1N1 strain.

Another aspect provides a composition for preparing an H5N6 recombinant influenza virus, including a polynucleotide encoding one or more proteins selected from the group consisting of: a hemagglutinin (HA) protein of influenza virus H5N6 strain, wherein the hemagglutinin protein is a hemagglutinin protein in which the $103^{rd}$ amino acid from the N-terminus is mutated in the amino acid sequence of SEQ ID NO: 1; neuraminidase (NA) of influenza virus H5N6 strain; polymerase subunit B2 (PB2) and matrix protein (M) of low pathogenic influenza virus; polymerase subunit B1 (PB1) and polymerase subunit A (PA) of influenza virus H1N1 strain; nucleocapsid (nucleoprotein: NP) of influenza virus H5N1 strain; and nonstructural protein (NS) of influenza virus H9N2.

Influenza virus H5N6 strain, hemagglutinin protein, neuraminidase, low pathogenic influenza virus, polymerase subunit B2, influenza virus H1N1 strain, polymerase subunit B1, polymerase subunit A, nucleocapsid, matrix protein, and nonstructural protein are the same as described above.

The polynucleotide may be a polynucleotide including a nucleic acid sequence encoding any one of the hemagglutinin protein, neuraminidase, polymerase subunit B2, polymerase subunit B1, polymerase subunit A, nucleocapsid, matrix protein, and nonstructural protein. The polynucleotide may be changed according to the codon usage frequency.

The polynucleotide may be included in a vector. The vector may be an expression vector. The vector may include a regulatory region (e.g., promoters, enhancers, and silencers) necessary for expression in animal cells. The polynucleotide may be operably linked to a regulatory region. The vector may further include an origin of replication, a poly A sequence, a multiple cloning site, a selection marker, and the like.

The vector may be a plasmid vector, a cosmid vector, a bacteriophage vector, or a viral vector. The viral vector may be an adenovirus vector, a retrovirus vector, or an adeno-associated virus vector.

Another aspect provides a method for preparing H5N6 recombinant influenza virus including incubating cells with the composition for preparing H5N6 recombinant influenza virus according to one aspect to transform the H5N6 recombinant influenza virus into the cells.

The cells may be cells capable of producing a recombinant virus. For example, the cells are 293T, MDCK, Vero, DF1, PK15, A549, and ST1 cells. The cells may be animal cells of algae. The cells may be cells of embryonic eggs of chicks or kidneys of chicken embryos.

The step of incubating cells with the composition for preparing H5N6 recombinant influenza virus may include adding the H5N6 recombinant influenza virus to an allantoic fluid of embryonated eggs, and culturing the allantoic fluid.

The transformation may be the introduction of a nucleic acid of the composition for preparing H5N6 recombinant influenza virus into cells. Transformation may be carried out by methods known in the art. For example, transformation may be performed by transduction, transfection, microinjection, lipofection, or electroporation.

The method may further include isolating the H5N6 recombinant influenza virus from the transformed cells.

Another aspect provides cells transformed with the composition for preparing H5N6 recombinant influenza virus according to one aspect.

The composition for preparing H5N6 recombinant influenza virus and transformation are as described above.

The cells may be cells capable of producing a recombinant virus. For example, the cells are 293T, MDCK, Vero, DF1, PK15, A549, and ST1 cells. The cells may be animal cells of algae. The cells may be cells of embryonic eggs of chicks or kidneys of chicken embryos.

Another aspect provides a vaccine composition including the H5N6 recombinant influenza virus according to one aspect.

The H5N6 recombinant influenza virus is as described above.

The vaccine composition may be for preventing flu or bird flu. The vaccine composition may be for administration to birds (e.g., chickens and ducks) or mammals (e.g., humans, pigs, dogs, cats, horses, cows, sheep, mice, and camels). The prevention refers to any action that suppresses the occurrence of diseases (e.g., flu and bird flu) caused by influenza virus or delays the onset of the diseases by administration of the vaccine composition.

The vaccine composition may include an effective amount of H5N6 recombinant influenza virus. The term "effective amount" refers to an amount sufficient to exhibit the effect of prophylaxis or treatment, when administered to a subject in need thereof. The effective amount may be appropriately selected by a person skilled in the art depending on the cells or subject selected. It may be determined according to the severity of disease, patient's age, weight, health, sex, patient's sensitivity to drugs, time of administration, route of administration and rate of excretion, duration of treatment, factors including drugs used in combination with or concurrently with the composition used, and factors well known in the other fields of medicine. The vaccine composition may be administered in an amount including about $1 \times 10^7$ to $1 \times 10^{11}$, $1 \times 10^8$ to $5 \times 10^{10}$, and $5 \times 10^8$ to $2 \times 10^{10}$ viral particles.

The vaccine composition may be a inactivated vaccine or live vaccine composition.

The vaccine composition may include a pharmaceutically acceptable carrier. The carrier is used in the sense of including an excipient, diluent or adjuvant. The carrier may be, for example, selected from the group consisting of lactose, dextrose, sucrose, sorbitol, mannitol, xylitol, erythritol, maltitol, starch, gum acacia, alginate, gelatin, calcium phosphate, calcium silicate, cellulose, methyl cellulose, polyvinyl pyrrolidone, water, physiological saline, a buffer such as PBS, methyl hydroxybenzoate, propyl hydroxybenzoate, talc, magnesium stearate, and mineral oil. The composition may include a filler, an anti-aggregating agent, a lubricant, a wetting agent, a flavoring agent, an emulsifying agent, a preservative, or a combination thereof.

The vaccine composition may be administered by a parenteral route (e.g., intravascular, intravenous, intraarterial, intramuscular, subcutaneous, etc.), oral, nasal, rectal, transdermal, or inhalation route through aerosol. The dosage of the vaccine composition may be, for example, about $1 \times 10^7$ to $1 \times 10^{11}$, $1 \times 10^8$ to $5 \times 10^{10}$, and $5 \times 10^8$ to $2 \times 10^{10}$ viral particles. The administration may be administered once a day, 2 to 24 times a day, 1 to 6 times a week, 1 to 3 times a month, or 1 to 12 times a year.

The vaccine composition may be formulated as an oral dosage form (e.g., powder, tablet, capsule, syrup, pill, or granule) or a parenteral dosage form (e.g., an injection). In addition, the composition may be prepared as a systemic formulation or a topical formulation.

The vaccine composition may be administered as an individual therapeutic agent or administered in combination with other therapeutic agents, and may be administered sequentially or simultaneously with a conventional therapeutic agent. In addition, it may be administered in a single unit or multiple units.

Another aspect provides a method for preventing flu or bird flu, including administering the vaccine composition according to one aspect to a subject.

The subject may be a bird (e.g., chicken and duck) or a mammal (e.g., human, pig, dog, and mouse).

The dosage of the vaccine composition varies depending on the condition and weight of the patient, the severity of the disease, the form of the drug, the route and duration of administration, but may be appropriately selected by those skilled in the art. The vaccine composition may be administered in an amount including about $1\times10^7$ to $1\times10^{11}$, $1\times10^8$ to $5\times10^{10}$, and $5\times10^8$ to $2\times10^{10}$ viral particles. The administration may be administered once a day, 2 to 24 times a day, 1 to 6 times a week, 1 to 3 times a month, or 1 to 12 times a year.

Advantageous Effects

In order to solve the problems of mammalian proliferation (possibility of obtaining pathogenicity), low stimulation ability of humoral immunity, and low heat resistance of the existing clade 2.3.4.4c H5N6 recombinant influenza A virus, the present invention introduces the H103Y mutation into the clade 2.3.4.4c HA gene, substitutes the PB2 gene of PR8 with the PB2 gene of 01310 to have mammalian pathogenicity, and thereby provides an mammalian non-pathogenic, highly immunogenic, and heat-resistant lade 2.3.4.4c H5N6 recombinant influenza A virus, and the recombinant virus provided in the present invention has high productivity and excellent efficacy and can be effectively used as a safe vaccine strain. In addition, by preparing a recombinant clade 2.3.4.4c H5N6 virus, in which the internal genes were substituted with the NP gene of SNU50-5 (SEQ ID NO: 5), which is a low pathogenic avian influenza virus, the NS gene of 0028 (SEQ ID NO: 6), and the M gene (SEQ ID NO: 7) of 01310, it was confirmed that the amount of virus released after attacking and inoculating the outdoor strain A/Mandarin duck/Korea/K16-187-3/2016 (H5N6), in which only the internal genes were different, was less, and thus, there is an effect of further increasing the immunogenicity of the recombinant vaccine, in which the internal genes are substituted.

DESCRIPTION OF DRAWINGS

FIG. 1 is a schematic diagram of the genome combination of an mammalian non-pathogenic, highly-productive-in-embryonated-egg, heat-resistant, and attenuated clade 2.3.4.4c H5N6 recombinant influenza A virus.

FIG. 2 is a result of confirming the proliferation of rH5N6-310PB2 and rH5N6-H103Y-310PB2 viruses in MDCK cells or A549 cells, which are mammalian cells.

FIG. 3 is a result of confirming the heat resistance of rH5N6-310PB2 and rH5N6-H103Y-310PB2 viruses.

FIG. 4 is a result of confirming the acid resistance of rH5N6-310PB2 and rH5N6-H103Y-310PB2 viruses.

FIG. 5 is a result of confirming the proteins of rH5N6-H103Y-310PB2 and rH5N6-310PB2 in embryonated eggs through SDS-PAGE to measure the antigen amount.

MODES OF THE INVENTION

Hereinafter, the present invention will be described in detail by exemplary embodiments. However, the following exemplary embodiments are only illustrative of the present invention, and the present invention is not limited by the following exemplary embodiments.

EXAMPLE 1

Construction and Characteristic Analysis of Recombinant Virus Having HA and NA Genomes of Highly Pathogenic H5N6 Avian Influenza Virus and PB2 Genome Segment of 01310

1-1. Construction of HA Genomic Plasmid with Mutated HA Protein of Influenza Virus By collecting the sequences of the HA and NA proteins of the highly pathogenic avian influenza virus H5N6 which was isolated in Korea, the HA and NA genome sequences with the highest coincidence were selected, and the cleavage site was changed to ASGR to synthesize the HA gene and the NA gene, from which pathogenicity was removed, respectively, and these were cloned into a Hoffman vector (Patent No. 0862758). In the case of the synthesized HA protein of H5N6, in order to substitute the $103^{rd}$ amino acid from histidine to tyrosine, the nucleotide constituting the codon of the corresponding amino acid in the HA genomic gene was substituted from CAC to TAC, and a set of about 30 bp complementary primers having the same sequence in both directions was prepared around the same. By using primers and the Muta-Direct Site Directed. Mutagenesis Kit (iNtRon Co., South Korea), the HA genome cloning vector plasmid of the synthesized H5N6 virus, in which the genome of the $103^{rd}$ amino acid portion of the HA protein was substituted from CAC to TAC, was constructed.

1-2. Production of Recombinant Virus

For the construction of recombinant influenza virus, Dr. Hoffman's reverse genetics vector system (Patent No. 0862758) was used.

Specifically, the Hoffman vector into which the HA and NA genome fragments of the synthesized highly pathogenic H5N6 avian influenza virus were cloned (Patent No. 0862758), the Hoffman vector into which the 01310 PB2 genome fragment was cloned (Patent No. 0862758), and the Hoffman vector into which PB1, PA, NP, M, and NS genome fragments of PR8 were cloned (Patent No. 0862758), the Hoffman vector into which the 01310 M genomic fragment was cloned, the Hoffman vector into which the SNU50-5 NP genomic fragment was cloned, and the Hoffman vector plasmid into which the 0028 NS fragment was cloned were prepared.

293T cells (Life Resources Center, KCTC) were suspended in DMEM (GIBCO BRL) medium containing 5% (v/v) FBS in a 6-well cell culture vessel, added to each well, and attached for 24 hours. After removing the medium, 0.8 mL of Opti-MEM medium (Invitrogen Co., USA) was added.

All of the 8 prepared plasmids were placed in an amount of 300 ng each in one 1.5 mL tube, and the Opti-MEM medium was added to final 2.5 µL. In another 1.5 mL tube, 6 µL of the plus reagent (Invitrogen Co., USA) and 69 µL of the Opti-MEM medium were added and mixed, and after mixing by adding to a 1.5 mL tube containing the plasmids, it was reacted at room temperature for 15 minutes.

After 15 minutes of the reaction, 4 µL of lipofectamine (Invitrogen Co.) and 96 µL of Opti-MEM were mixed, and by taking 100 µL, it was added to the tube with the plasmids, followed by further reaction for 15 minutes. 200 µL, of the obtained reaction product was added to each well containing the 293T cells. After incubating the 6-well culture vessel at 5% CO2 and 37° C. for 20 hours, 10 µg of trypsin (2.5

μg/μL) per well and 1 mL of the opti-MEM medium were added, and the supernatant was harvested after 24 hours to inoculate 200 μL of the harvested stock solution into 10 to 11-day-old SPF embryonated eggs (Sunrise Co., NY) by the allantoic route. After incubating the inoculated embryonated eggs at 37° C. for 3 days, the allantoic fluid was harvested to determine whether hemagglutination occurred, and as a result, all showed positive hemagglutination. The hemagglutination titer of this recombinant virus was measured and diluted 100 times, and the virus (E2) proliferated in embryonated eggs by the same method was stored at −70° C. and used in the experiment.

TABLE 1

| Recombinant virus | HA | NA | PB2 | PB1 | PA | NP | M | NS |
|---|---|---|---|---|---|---|---|---|
| rH5N6 | H5 | N6 | PR8 | PR8 | PR8 | PR8 | PR8 | PR8 |
| rH5N6-H103Y | H5-H103Y | N6 | PR8 | PR8 | PR8 | PR8 | PR8 | PR8 |
| rH5N6-310PB2 | H5 | N6 | 01310 | PR8 | PR8 | PR8 | PR8 | PR8 |
| rH5N6-IG | H5 | N6 | 01310 | PR8 | PR8 | 50-5 | 01310 | 0028 |
| rH5N6-H103Y-310PB2 | H5-H103Y | N6 | 01310 | PR8 | PR8 | PR8 | PR8 | PR8 |
| rH5N6-H103Y-IG | H5-H103Y | N6 | 01310 | PR8 | PR8 | 50-5 | 01310 | 0028 |

1-3. Measurement of Viral Titer

In order to measure the proliferation titer (50% embryo infection dose, $EID_{50}$/mL) of the recombinant viruses (E2) in chicken embryos, each of the recombinant viruses was diluted in decimal by $10^{-1}$ to $10^{-9}$ with a phosphate buffer solution and inoculated by 100 μL into five 10 to 11-day-old SPF embryonated eggs for each dilution factor by the allantoic route. Then, after 3 days of incubation, the allantoic fluid was harvested, and the viral titer ($EID_{50}$/mL) was measured according to the calculation formula of the Spearman-Karber method by determining whether hemagglutination occurred with red blood cells of the chicken.

1-4. Comparison of Proliferative Properties in 10-Day-Old Embryonated Eggs

Based on the viral titer ($EID_{50}$/mL (log 10)) obtained in Example 1-3 above, the virus at 100 $EID_{50}$ was inoculated by 100 μL into each of five 10-day-old embryonated eggs by the allantoic route. Then, after 3 days of incubation, the allantoic fluid was harvested, and $EID_{50}$/mL was measured in the same manner as above, and the result of comparing the proliferative properties in embryonated eggs is shown in Table 1 below. Looking at the viral titer ($EID_{50}$/mL (log 10)), it was confirmed that the proliferation titer in embryonated eggs showed high proliferation of more than $10^{9.0}$ $EID_{50}$/mL in all four viruses, rH5N6, rH5N6-H103Y, rH5N6-310PB2, and rH5N6-H103Y-310PB2. The rH5N6-IG and rH5N6-H103Y-IG viruses with modified NP, M, and NS genes also showed proliferative properties of about $10^{9.0}$ $EID_{50}$/mL.

TABLE 2

| Recombinant virus | $EID_{50}$/mL (log 10) |
|---|---|
| rH5N6 | 9.08 ± 0.14 |
| rH5N6-H103Y | 9.03 ± 0.31 |
| rH5N6-310PB2 | 9.33 ± 0.29 |
| rH5N6-IG | 9.25 ± 0.25 |
| rH5N6-H103Y-310PB2 | 9.58 ± 0.14 |
| rH5N6-H103Y-IG | 8.92 ± 0.38 |

1-5. Confirmation of Proliferation of Recombinant Virus in Mammalian Cells

In order to compare whether each recombinant virus proliferates in mammalian cells, the growth curves in the Madin-Darby Canine Kidney (MDCK) cell line and the A549 cell line were determined. In the case of the MDCK cell line, 10% fetal bovine serum (FBS) was added to Dulbecco's Modified Eagle Medium (DMEM) (Life Technologies Co., CA, USA) and maintained, and in the case of the A549 cell line, 10% FBS was added to DMEM/F12 (Life Technologies Co., CA, USA) medium and maintained. Two types of the cell lines were each formed into a mono-layer on a 12-well cell culture plate, and then, $5×10^5$/0.5 mL of each recombinant virus was inoculated, and 100 μL of the supernatant was obtained every 0, 24, 48, and 72 hours. The obtained supernatant was diluted in decimal by $10^{-1}$ to $10^{-9}$ and inoculated into MDCK cells in which a mono-layer was formed in a 96-well cell culture plate, and the Tissue Culture infectious Dose ($TCID_{50}$/0.1 mL) was measured, and the result is shown in FIG. 2. In both MDCK cells and A549 cells, it was confirmed that rH5N6 proliferated at the level of rPR8, whereas rH5N6-H103Y proliferated similarly in MDCK cells, but the proliferation decreased in A549 cells, and rH5N6-310PB2 and rH5N6-H103Y-310PB2 could not proliferate in both of the two cells.

1-6. Comparison of Heat Resistance

Figure 3:
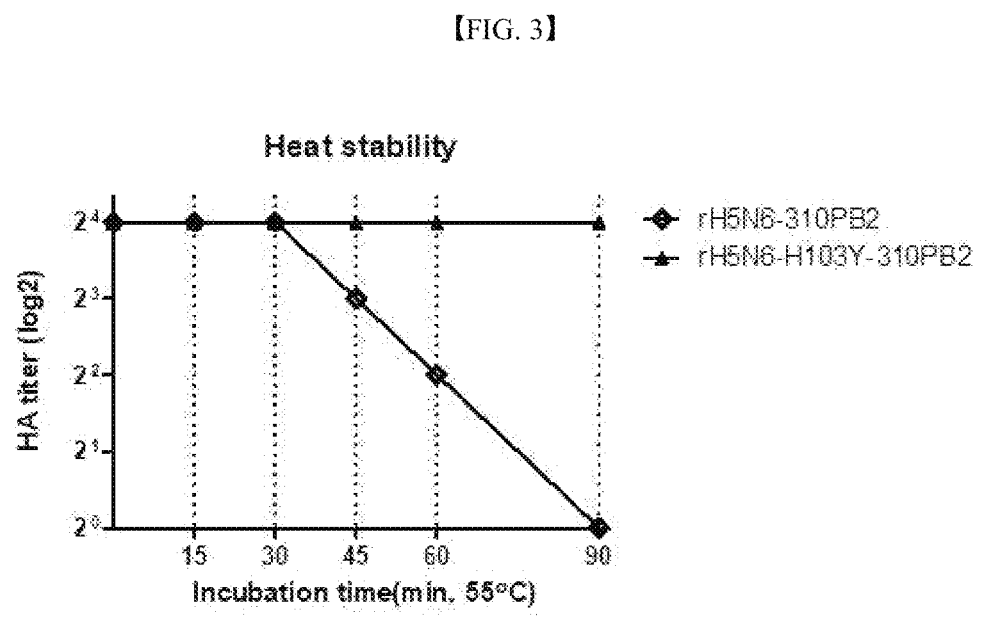

In order to confirm whether H103Y actually increases heat resistance and increases proliferation in embryonated eggs, mammalian cell lines and mice, the rH5N6-310PB2 and rH5N6-H103Y-310PB2 viruses were treated at 55° C. for 0, 15, 30, 45, 60, and 90 minutes, respectively, and the result of comparing the HA titers through the HA, test is shown in FIG. 2. Unlike rH5N6-310PB2, in the case of rH5N6-H103Y-310PB2, it was confirmed that the HA protein was stable up to 90 minutes to increase heat resistance (FIG. 3).

1-7. Comparison of Acid Resistance

In order to observe the effect of H103Y on acid resistance, after rH5N6 and rH5N6-H103Y viruses were reacted for 1 hour in various environments from pH 5.0 to pH 6.0, respectively, these were inoculated into mammalian cell lines and eggs, and as a result, it was confirmed that rH5N6-H103Y lost its maturity at low pH and lost proliferation at pH 5.2 or less in MDCK cells, and at pH 5.0, it lost proliferative properties such that it was inactivated more easily in an acidic environment. It is known that influenza virus isolated from humans undergoes fusion of the HA protein at a lower pH, and avian influenza exhibits activity at a relatively high pH, and it was found that the rH5N6-H103Y-310PB2 virus had a lower risk of transmission to the human body because the activity was removed at low pH (FIG. 4).

1-8. Comparison of Antigen Amount

In order to determine whether the antigen amount increases when H103Y is applied, the same amounts of the rH5N6-310PB2 and rH5N6-H103Y-310PB2 viruses were separated by ultracentrifugation of the allantoic fluid, and the total amount of virus protein was measured through the Bicinchonic Acid (BCA) assay, and the amount of each virus constituent protein was compared through SDS-PAGE. Whereas rH5N6-H103Y-310PB2 had a slightly lower $EID_{50}/1$ mL than that of rH5N6-310PB2, which is the proliferation titer of in embryonated eggs, it was confirmed that the antigen amount compared to the proliferation titer was more excellent because the amounts of the HA titer and the total virus protein and the amount of each protein in SDS-PAGE were more excellent. (FIG. 5).

TABLE 3

| | $EID_{50}/1$ mL (log 10) | HA titer | Total protein amount of virus (μg/mL) |
|---|---|---|---|
| rH5N6-310PB2 | 9.92 ± 0.38 | 64.00 ± 0.00 | 1325.42 |
| rH5N6-H103Y-310PB2 | 9.42 ± 0.14 | 107.63 ± 0.89 | 2008.75 |

1-9. Comparison of Stimulation Ability of Humoral Immunity

The rH5N6-H103Y-310PB2 had a more excellent antigen content at similar proliferative titers compared to rH5N6-310PB2, and when it was actually inactivated and inoculated into chickens and ducks with an oil emulsion vaccine, it was determined whether the antibody formation was further increased. When inoculated to 3-week-old chickens, the rH5N6-H103Y-310PB2-inoculated group at the 3$^{rd}$ week of inoculation showed an average of 172.3, about twice as much antibody titer compared to the rH5N6-310PB2-inoculated group, and while the degree was low in ducks, rH5N6-H103Y-310PB2 showed a better ability to stimulate humoral immunity as an inactivated oil emulsion vaccine.

TABLE 4

| Vaccination age, species | Inactivated vaccine | Antibody titer (geometric mean, 95% confidence interval) | | |
|---|---|---|---|---|
| | | Vaccination week 0 | Vaccination week 3 | Vaccination week 4 |
| 3 weeks old, chicken | rH5N6-310PB2 | <2 | 98.70 (64.13-151.9) | 90.51 (42.38-193.3) |
| | rH5N6-H103Y-310PB2 | <2 | 172.3 (88.28-356.4) | 152.2 (68.06-340.4) |
| | Negative control | <2 | <2 | <2 |

TABLE 4-continued

| Vaccination age, species | Inactivated vaccine | Antibody titer (geometric mean, 95% confidence interval) | | |
|---|---|---|---|---|
| | | Vaccination week 0 | Vaccination week 3 | Vaccination week 4 |
| 2 weeks old, duck | rH5N6-310PB2 | <2 | 14.86 (6.95-22.77) | 12.00 (7.22-16.78) |
| | rH5N6-H103Y-310PB2 | <2 | 20.16 (9.49-42.83) | 18.66 (9.84-35.41) |
| | Negative control | <2 | <2 | <2 |

1-10. Comparison of Stimulation Ability of Cellular Immunity

When rH5N6-IG was inoculated into embryonated eggs with a similar proliferative titer compared to rH5N6-310PB2, the obtained antigen amount was lower, and it was actually inactivated, resulting in lower antibody formation when inoculated into chickens as an oil emulsion vaccine. When inoculated to 3-week-old chickens, the rH5N6-310P132-inoculated group showed an average of 118.5 at the 3$^{rd}$ week of inoculation, and in the case of the rH5N6-IG-inoculated group, it was 64, showing an antibody titer about twice as low. On Days 1, 3, 5, and 7 after attacking and inoculating with the outdoor strain H5N6 virus, the excretion of the virus into the throat cavity and total excretion cavity was terminated earlier, and it was confirmed that the antibody formation ability was low when the internal genes were substituted with the genome fragments derived from avian influenza virus, but viral clearance was performed more effectively.

TABLE 5

| Vaccination age, species | Inactivated vaccine | Antibody titer (geometric mean, 95% confidence interval) | | |
|---|---|---|---|---|
| | | Vaccination week 0 | Vaccination week 3 | Vaccination week 4 |
| 3 weeks old, chicken | rH5N6-310PB2 | <2 | 118.5 (78.14-179.7) | 118.5 (72.28-194.3) |
| | rH5N6-IG | <2 | 64.00 (43.91-93.28) | 80.63 (55.32-117.5) |
| | Negative control | <2 | <2 | <2 |

TABLE 6

| Vaccination age, species | Inactivated vaccine | Virus release rate | | | | | | | |
|---|---|---|---|---|---|---|---|---|---|
| | | Throat cavity | | | | Total excretion cavity | | | |
| | | Day 1 | Day 3 | Day 5 | Day 7 | Day 1 | Day 3 | Day 5 | Day 7 |
| 3 weeks old, chicken | rH5N6-310PB2 | 2/9 | 7/9 | 4/9 | 3/9 | 2/9 | 6/9 | 4/9 | 2/9 |
| | rH5N6-IG | 4/9 | 4/9 | 4/9 | 0/9 | 1/9 | 5/9 | 4/9 | 0/9 |
| | Negative control | 9/9 | 9/9 | Dead | | 7/9 | 9/9 | Dead | |

[Depositary Institution]
Name of depositary institution: Korean Collection for Type Cultures, Korea Research Institute of Bioscience and Biotechnology, located at 181, Ipsin-gil, Jeongeup-si, Jeolllabuk-do 56212; Republic of Korea
Accession number: KCTC14391BP
Date of deposit: Nov. 27, 2020

Name of depositary institution: Korean Collection for Type Cultures, Korea Research Institute of Bioscience and Biotechnology, located at 181, Ipsin-gil, Jeongeup-si, Jeolllabuk-do 56212; Republic of Korea
Accession number: KCTC14261BP
Date of deposit: Aug. 4, 2020

The invention claimed is:

1. An H5N6 recombinant influenza virus deposited as Accession No. KCTC14261BP, comprising one or more proteins selected from the group consisting of:

a hemagglutinin (HA) protein of influenza virus H5N6 strain, wherein the hemagglutinin protein is a hemagglutinin protein, histidine (H), in which the 103$^{rd}$ amino acid from the N-terminus is mutated in the amino acid sequence of SEQ ID NO: 1 to tyrosine (Y);

neuraminidase (NA) of H5N6 strain;

polymerase subunit B2 (PB2) of low pathogenic influenza virus;

polymerase subunit B1 (PB1) of influenza virus H1N1 strain;

polymerase subunit A (PA) of influenza virus H1N1 strain;

nucleocapsid (nucleoprotein: NP) of influenza virus H1N1 strain or influenza virus H5N1 strain;

matrix protein (matrix: M) of influenza virus H1N1 strain or low pathogenic influenza virus; and nonstructural protein (NS) of influenza virus H1N1 strain or influenza virus H9N2.

2. The H5N6 recombinant influenza virus of claim 1, wherein the low pathogenic influenza virus is low pathogenic influenza virus 01310 strain.

3. The H5N6 recombinant influenza virus of claim 1, wherein the influenza virus H1N1 strain is A/Puerto Rico/8/34(PR8).

4. The H5N6 recombinant influenza virus of claim 1, wherein the influenza virus H5N1 strain is A/wild duck/Korea/SNU50-5/2009.

5. The H5N6 recombinant influenza virus of claim 1, wherein the influenza virus H9N2 strain is A/chicken/Korea/KBNP-0028/00.

6. A vaccine composition, comprising the H5N6 recombinant influenza virus of claim 1.

* * * * *